United States Patent [19]

Ohshima et al.

[11] Patent Number: 4,546,077
[45] Date of Patent: Oct. 8, 1985

[54] LEUCINE DEHYDROGENASE AND A PROCESS FOR PRODUCTION THEREOF

[75] Inventors: Toshihisa Ohshima; Kenji Soda, both of Kyoto, Japan

[73] Assignee: Unitika Ltd., Hyogo, Japan

[21] Appl. No.: 525,905

[22] Filed: Aug. 24, 1983

[30] Foreign Application Priority Data

Aug. 24, 1982 [JP] Japan .............................. 57-147399
Oct. 12, 1982 [JP] Japan .............................. 57-179570

[51] Int. Cl.$^4$ .......................... C12Q 1/32; C12N 9/06; C12R 1/07
[52] U.S. Cl. ...................................... 435/26; 435/191; 435/832
[58] Field of Search .......................... 435/191, 26, 832

[56] References Cited

U.S. PATENT DOCUMENTS 4,179,335 12/1979 Long et al. .............................. 435/99
4,331,762  5/1982 Nakajima et al. ...................... 435/190
4,342,827  8/1982 Atkinson et al. ...................... 435/26

FOREIGN PATENT DOCUMENTS 54-119290 9/1979 Japan .................................... 435/26
58-212782 12/1983 Japan .................................... 435/191

OTHER PUBLICATIONS

Zink et al., "L-Leucine Dehydrogenase (Bacillus Cereus) in Methods in Enzymology 17A, 799–803, (1970).

*Primary Examiner*—Lionel M. Shapiro
*Attorney, Agent, or Firm*—Sughrue, Mion, Zinn Macpeak & Seas

[57] ABSTRACT

Leucine dehydrogenase is disclosed which retains 80% or more of the activity even after it is incubated in a buffer solution at about 70° C. for 10 minutes, as compared to the activity prior to incubation. A process for producing a heat resistant leucine dehydrogenase is also disclosed. The process comprises culturing a microorganism having an optimum growth temperature of 50° to 85° C. and harvesting the leucine dehydrogenase from the culture and a composition of assaying for leucine aminopeptidase (LAP) comprising the heat resistant leucine dehydrogenase.

The leucine dehydrogenase can be stored for a long period of time and thus very effective for investigations in biochemistry, food analysis and clinical test. Further the composition provides extremely easy assay for the LAP activity in high accuracy with good reproducibility which is an important item in clinical test.

19 Claims, 2 Drawing Figures

LEUCINE DEHYDROGENASE AND A PROCESS FOR PRODUCTION THEREOF

FIELD OF THE INVENTION

The present invention relates to novel and useful leucine dehydrogenase and a process for production thereof as well as a composition for assaying leucine aminopeptidase (hereafter simply referred to as LAP).

BACKGROUND OF THE INVENTION

Recently, attention has been given to enzymes due to their reaction specificities, substrate specificities and stereo specificities. Enzymes have been widely utilized as catalysts for medical analysis, food analysis, and the like. Among them, LAP, which is an enzyme present in blood serum, is known to be closely related to pancreas cancer, transfer of malignant tumors to the liver, diseases in the hepatic duct, etc. Accordingly, assay for LAP activity is an important inspection item in a clinical test. In assaying for the LAP activity, a method using leucine dehydrogenase has recently been utilized. The leucine dehydrogenase has been found useful due to enzymes' excellent specificities as mentioned above.

A method of assay for a trace amount using an enzyme generally involves the foregoing advantages. However, the enzyme is generally very unstable so that its catalytic activity is lost at room temperature within from several days to several weeks. This unstability is thus a serious bar with respect to assaying for a trace amount of a substance using an enzyme. Known leucine dehydrogenase is also unstable; for example, leucine dehydrogenase obtained from *Bacillus sphaericus* as described in *J. Biol. Chem.*, vol. 253, page 5719 (1978) generally loses its activity in an aqueous solution (room temperature) within 1 to 3 weeks. Thus leucine dehydrogenase encounters serious disadvantages in lacking heat stability and stability over long periods of time. To best exhibit the advantages of assaying using leucine dehydrogenase it has been strongly desired to develop leucine dehydrogenase having stability to heat without losing its activity at room temperature over long periods of time.

On the other hand, in assaying for the LAP activity conventionally applied, a method which comprises using L-leucyl-β-naphthylamide as a substrate and colorimetrically determining the formed β-naphthylamine with p-dimethylaminobenzaldehyde, a method which comprises using L-leucyl-p-nitroanilide as a substrate and colorimetrically determining the formed p-nitroaniline, etc. are known. However, these methods are unsatisfactory in terms of specificity, etc. and were not suited for accurate measurement.

In recent years, assay methods utilizing the specificity of enzymes have also been widely adopted in the field of clinical tests. With respect to eliminating the foregoing disadvantages, these so called enzymatic methods are extremely effective. An enzymatic method has also been proposed with respect to the assay of LAP activity as shown in Japanese Patent Publication 20840/81. This method comprises reacting leucine dehydrogenase with L-leucine formed from a substrate of LAP and either measuring the amount of change of NAD+present to NADH at an absorbancy of 340 nm, or, conjugating with a dye forming reaction and measuring with an absorbancy at the visible regions. However, this method is not practically used. That is, in this method, enzyme derived from the aforesaid *Bacillus cereus, Bacillus subtilis* or *Bacillus sphaericus* as sources is employed as leucine dehydrogenase and for this reason, it is possible to measure the LAP activity. However, there are problems in that data obtained are liable to be scattered, reproduction is poor, stability during storage is poor, enzyme per se is obtained only with difficulty and thus extremely expensive, etc. These problems become a bar to practical use.

SUMMARY OF THE INVENTION

An object of the present invention is to provide leucine dehydrogenase having properties that are stable to heat without losing its activity for a long period of time, and a process for the production thereof.

Another object of the present invention is to provide a composition of assaying for LAP which is an important item in clinical tests.

As a result of extensive investigations to achieve the foregoing objects, the present inventors have found that leucine dehydrogenase having the aforesaid properties is present in microorganism which grows at an optimum growth temperature of 50° to 85° C. and have accomplished the present invention. The present inventors have further found that by the use of this leucine dehydrogenase, a composition of assaying for LAP which provides extremely easy assay in high accuracy with good reproducibility is obtained and have accomplished the present invention.

That is, the present invention is directed to leucine dehydrogenase having a property wherein about 80% or more of the activity is retained as compared to the activity prior to treatment, even after it is incubated in a buffer solution at about 70° C. for 10 minutes. The invention also relates to a process for producing leucine dehydrogenase which comprises culturing a microorganism having an optimum growth temperature of 50° to 85° C. and harvesting from the culture leucine dehydrogenase having a property wherein about 80% or more of the activity is retained after incubating in a buffer solution at about 70° C. for about 10 minutes as compared to the activity prior to the treatment. The present invention is further directed to a composition of assaying for LAP comprising leucine dehydrogenase, characterized in that the leucine dehydrogenase is leucine dehydrogenase having a property in which about 80% or more of the activity is retained after incubating in a buffer solution at about 70° C. for about 10 minutes, as compared to the activity prior to the treatment.

The leucine dehydrogenase in accordance with the present invention is very stable to heat and can thus be stored for a long period of time after isolation, as compared to conventional leucine dehydrogenase. For this reason, the leucine dehydrogenase is very effective for investigations in biochemistry, food analysis and clinical tests. Further the composition of the present invention provides extremely easy assay for the LAP activity with high accuracy and good reproducibility which is an important item in clinical tests.

DESCRIPTION OF THE INVENTION

Figure 1:
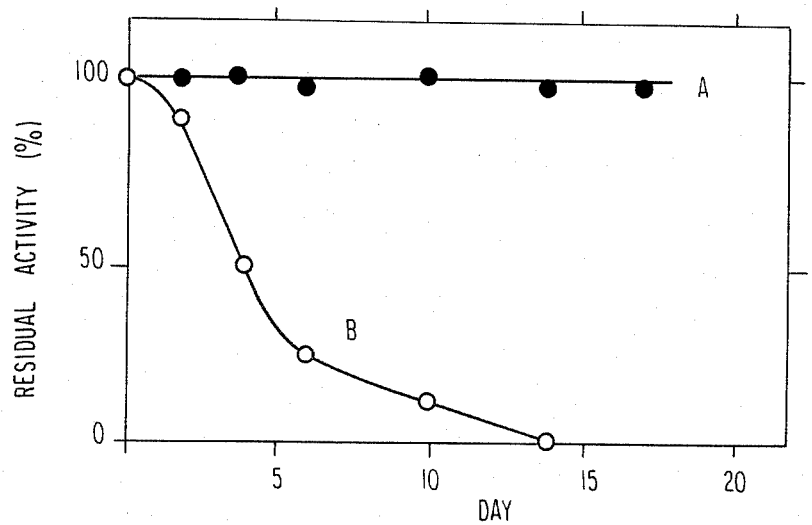
FIG. 1 is a graph showing the residual activity of the leucine dehydrogenase in accordance with the present invention (curve A) and a leucine dehydrogenase obtained from *Bacillus sphaericus* (curve B) after being allowed to stand at 4° to 8° C.

The leucine dehydrogenase referred herein is an enzyme which acts as a catalyst in deamination reaction of L-leucine in coexistence of oxidized type nicotinamide adenine dinucleotide (NAD+) to form α-ketoisocaproic acid, ammonia and reduced type nicotinamide adenine dinucleotide as a reaction product.

The leucine dehydrogenase in accordance with the present invention possesses a property that by incubating in a buffer solution at about 70° C. for about 10 minutes, 80% or more of the original activity of the leucine dehydrogenase is retained. Preferably about 90% or more of the original activity is retained and most preferably about 100% of the original activity is retained. The leucine dehydrogenase of the present invention possesses an excellent property in which the activity is retained by about 80% or more, particularly after incubating in a buffer solution at about 70° C. for about 30 minutes, as compared to the activity prior to the incubation. The concentration and pH of the buffer solution are not particularly limited but the concentration is generally in the range of 5 mM to 500 mM and the pH generally in the range of 6 to 10. In the present invention, it is particularly preferred that a 10 mM phosphate buffer solution (pH 7.2) containing 0.01 vol% of 2-mercaptoethanol be employed.

To prepare the leucine dehydrogenase of the present invention, it is preferred that, for example, a microorganism having the optimum growth temperature of 50° to 85° C. be cultured and the leucine dehydrogenase be harvested from the culture. Any microorganisms can be used as microorganisms having the optimum growth temperature of 50° to 85° C. as long as they are capable of producing the leucine dehydrogenase of the present invention and typical examples of such microorganisms include the genus *Bacillus* such as *Bacillus stearothermophilus*, *Bacillus thermoproteoliticus*, *Bacillus acidokaludarius*, the genus *Thermoactinomyces*, the genus *Thermus*, the genus *Thermomicrobium*, the genus *Carderia*, etc. Of these microorganisms, those belonging to the genus *Bacillus* are particularly preferred. Particularly preferred is *Bacillus stearothermophilus*. Specific examples of the *Bacillus stearothermophilus* include ATCC 7953, 7954, 8005, 10194 and 12980 and NCA 1503, etc.

In a nutrient medium which is employed in culturing microorganisms in the present invention, examples of carbon sources which can be employed include glucose, sucrose, fructose, starch hydrolysates, molasses, sugars from sulfite pulp wastes; organic acids such as acetic acid, lactic acid, etc.; and further alcohols, oils and fats, fatty acids, glycerine, etc. which can be utilized by the microorganisms used. Examples of nitrogen sources which can be employed include inorganic or organic compounds such as ammonium sulfate, ammonium chloride, ammonium phosphate, ammonia, amino acids, pepton, meat extracts, yeast extracts, etc. Examples of inorganic salts which can be employed include salts of potassium, sodium, phosphoric acid, zinc, iron, magnesium, manganese, copper, calcium, cobalt, etc. If necessary, trace amounts of metal salts, corn steep liquor, vitamins, nucleic acids, etc. may also be used and conventional nutrient media for bacteria can be used.

Using these media, the bacteria belonging to the genus *Bacillus* may be aerobically cultured at temperatures of 20° to 80° C., preferably 40° to 70° C., most preferably 55° C. for about 2 to about 16 hours. Further on an industrial scale, a continuous culture method in which culture is continuously carried out, while controlling dilution rate (a value obtained by dividing a rate of feeding a medium solution to a fermentation tank or a rate simultaneously withdrawn from the fermentation tank by an amount of a culture solution in the fermentation tank) within a range of 0.3 to 1.0, preferably the range of 0.5 to 1.0, most preferably the range of 0.7 to 1.0 of the maximum specific growth rate of the strain used, can also be adopted.

Next, the leucine dehydrogenase of the present invention is harvested from the culture product; the leucine dehydrogenase can be harvested at all of the stages from the culture product, viable bacteria isolated, treated matters of the isolated bacteria, crude anzyme, purified enzyme, etc. For purification, conventional methods for purification of enzyme can be employed. That is, after collecting bacteria by centrifugation, etc., the bacteria is sheared by means of a manton gaulin, a dynomill, a French press, a ultrasonic treatment, grinding in a glass mortar, etc. Then, cell fragments are removed by centrifugation to obtain a cell extract. The cell extract is treated with streptomycin sulfate or protamine sulfate further followed by precipitation with polyethylene glycol, precipitation with acetone, heat treatment, etc. For purification, chromatography techniques, e.g., ion exchange chromatography using DEAE-cellulose column, etc., adsorption chromatography using a hydroxyappatite column, etc., gel filtration chromatography such as Sephadex chromatography, etc. can be used in combination. The leucine dehydrogenase of the present invention can thus be isolated and purified.

Next, physico-chemical properties of the thus obtained leucine dehydrogenase of the present invention are shown below, wherein the leucine dehydrogenase was obtained from *Bacillus stearothermophilus*.

(1) Activity:

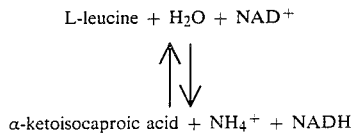

L-leucine + H₂O + NAD⁺ ⇌ α-ketoisocaproic acid + NH₄⁺ + NADH

The leucine dehydrogenase catalyzes the above reaction.

(2) Substrate Specificity:

The Michaellis constants (Km values to L-leucine and Nad are about 1.5 mM and about 0.4 mM, respectively. It reacts with L-valine and L-isoleucine, in addition to L-leucine.

(3) Optimum pH:

about pH 11 (55° C.)

(4) Stable pH Range:

Inactivation hardly occurs at pH 5.5 to 10.5 when incubated at 55° C. for 5 minutes.

(5) Optimum Temperature Range:

Range of 25° to 70° C. at pH 11

(6) Heat Resistance:

It is stable against incubation at 70° C. for 30 minutes.

(7) Molecular Weight:

It was calculated to be about 290,000 to 310,000 based on gel chromatography using Toyopearl 55-F (trademark, manufactured by Toyo Soda Co., Ltd.).

(8) Measurement of Titer:

A solution mixture containing 1.25 mM NAD and 10 mM L-leucine in a 0.1 1M glycine-KCl-KOH buffer solution having pH 11 was prepared. A suitable amount of a leucine dehydrogenase was added to the solution mixture and the increment of a reduced type NAD per unit time at 55° C. was measured as an increment of the absorbancy at 340 nm. The amount of the enzyme which made it possible to increase the absorbancy of 1μ mole of NADH at 340 nm per minute was set at 1 unit.

(9) Purity:

The purified enzyme moved to the cathode and showed a single protein band in 7.5% polyacrylamide disc gel electrophoresis at pH 9.4.

(10) Elemental Analysis:

No elemental analysis was measured.

(11) Crystal Structure:

It is unclear because it has not yet been obtained as crystals.

The leucine dehydrogenase of the present invention is extremely stable to heat and can be stored, after isolation of the enzyme, over a long period of time, as compared to the prior art leucine dehydrogenase. For this reason, the leucine dehydrogenase of the present invention is very useful in the fields of biochemical study, food and clinical tests: For example, the content of L-leucine in a specimen solution can be measured with good accuracy, using a reaction solution comprising the leucine dehydrogenase of the present invention and NAD. The assay of L-leucine can be used for measurement of the LAP activity which forms L-leucine from L-leucinamide. The measurement of leucine aminopeptidase activity in serum is utilized for diagnosis of liver diseases, bile excretion disorders, etc. and is an important item among clinical investigations.

Next, the composition of the present invention will be explained below. First, LAP is an enzyme which acts with a peptide having an L-leucyl group at the amino terminal to render L-leucine free.

Accordingly, LAP is reacted with the combination of the leucine dehydrogenase and $NAD^+$ using such a peptide as a substrate, whereby the formed L-leucine is converted into α-ketoisocaproic acid and ammonia and $NAD^+$ is reduced to NADH. The measurement of the absorbance of NADH at 340 nm provides a quantitative determination of the LAP activity. Further when NADH is conjugated with appropriate electron transfer substances, such as phenazine methosulfate, phenazine methosulfate of reduced type is formed; the reduced type in turn conjugates with a tetrazolium salt to form bluish purple or red purple formazan. Accordingly, the activity of LAP can be quantitatively determined also by colorimetrically determining the formazan. In this case, also when diaphorase is reacted in place of phenazine methosulfate, it is possible to colorimetrically determine formazan. All substrates can theoretically be used as long as they are peptides having an L-leucyl group at the amino terminal thereof. However, from a practical standpoint, specific useful examples include L-leucinamide, L-leucyl glycine, L-leucyl leucine, L-leucyl valine, L-leucyl alanine, L-leucyl glycylglycine, L-leucyl leucylleucine, etc.

When using the composition of the present invention, it is preferred that the reaction temperature be in the range of 20° to 40° C.; the composition can thus be effectively used at temperatures of 30° C. and 37° C. which are conventionally employed in clinical tests. In particular, it was first presumed that enzymes produced by microorganisms which had the optimum growth temperature of 50° to 85° C. would not suit for use at such normal temperatures. However, it has been found that such use is actually extremely suitable. It is preferred that the pH of the reaction be in the range of 7 to 9, particularly around 8.

As a specific amount of the composition of the present invention to be employed, it is sufficient that the composition contains in the range of 1 U/ml to 10 U/ml of leucine dehydrogenase, in the range of 1 mM to 50 mM of the substrate and in the range of 1 mM to 10 mM of $NAD^+$. When performing the measurement as a colorimetric system, it is sufficient that phenazine methosulfate be used in the range of 1 μg/ml to 50 μg/ml and the tetrazolium salt be used in the range of 10 μg/ml to 500 μg/ml.

The composition of the present invention provides easy assay for the LAP activity in an extremely simple manner with high accuracy and good reproducibility, which is an important item in clinical tests. Further the composition in accordance with the present invention is inexpensive and provides high practicability.

Hereafter the present invention will be specifically explained with reference to the examples. However, the scope of the invention is not limited to the examples.

EXAMPLE 1 AND COMPARATIVE EXAMPLE 1

After sterilizing 3 l of a medium adjusted to pH 7.2 comprising 10 g/l of polypepton, 2.5 g/l of yeast extracts, 2 g/l of meat extract, 2 g/l of glycerin, 5 g/l of sodium chloride, 2 g/l of dipotassium phosphate, 2 g/l of monopotassium phosphate, 0.1 g/l of magnesium sulfate, and 4 μg/l of biotin with heating at 120° C. for 10 minutes, *Bacillus stearothermophilus ATCC* 12980 strain was inoculated followed by aerobic cultivation at 55° C. for 15 hours. After cultivation, the bacteria was harvested by centrifuge to obtain 11 g of wet bacteria.

The thus obtained bacteria was ground for about 20 minutes in a mortar together with about 30 g of aluminum oxide powders. Then, 50 ml of a 0.6 M phosphate buffer solution containing 0.01 v/v% of 2-mercaptoethanol was added to the mixture. By subjecting the mixture to centrifugation, aluminum oxide and cell segments were removed to obtain a crude extract containing the leucine dehydrogenase.

Polyethylene glycol (average molecular weight, 7,500) was added to the crude extract at a final concentration of 9% (w/v). After stirring the mixture, the formed precipitates were removed by centrifugation to obtain the supernatant (a crude enzyme liquid). The thus obtained crude enzyme liquid was passed through a DEAE cellulose column which had previously been equilibrated with a 10 mM phosphate buffer solution (pH 7.2) containing 0.01 vol% of 2-mercaptoethanol. When the elution was carried out with the aforesaid buffer solution added sodium chloride, the desired leucine dehydrogenase was eluted out at around 0.35 M of the sodium chloride concentration.

The fractions were collected and solid ammonium sulfate was gradually added thereto until the system reached 30% saturation (4° C.). The formed precipitates were removed by centrifugation. Solid ammonium sulfate was again gradually added to the resulting supernatant until the system reached 60% saturation (4° C.). The formed precipitates were collected by centrifugation and gel chromatography on Sephadex G-150 was performed using a 10 mM phosphate buffer solution (pH 7.2) containing 0.01 vol% of 2-mercaptoethanol and 0.1 M potassium chloride as an eluting solution.

Then, the eluted active fractions were dialyzed with a 2 mM phosphate buffer solution containing 0.01 v/v% 2-mercaptoethanol. Thereafter, the solution was passed through a hydroxyappatite column which had previously been equilibrated with the same buffer solution. When the concentration of the buffer solution was continuously elevated to 100 mM, the desired leucine dehydrogenase was eluted out around 20 to 35 mM of the buffer concentration. The fractions were collected and passed through a DEAE-cellulose column which had previously been equilibrated with a 10 mM phosphate buffer solution (pH 7.2) containing 0.01 vol% of 2-mercaptoethanol. When the elution was carried out with the aforesaid buffer solution added sodium chloride, the desired leucine dehydrogenase was eluted out around 0.2 to 0.25 M of the sodium chloride concentration. Further, the fractions were collected and solid ammonium sulfate was added thereto until the system reached 70% saturation (4° C.). The formed precipitates were collected by centrifugation. Then gel chromatography on Sephadex G-150 was carried out using a 10 mM phosphate buffer solution (pH 7.2) containing 0.01 vol% of 2-mercaptoethanol and 0.1M of potassium chloride as an eluting solution.

As a result, 1.2 mg of purified leucine dehydrogenase was obtained.

The thus obtained leucine dehydrogenase moved to the cathode and showed a single protein band in 7.5% acrylamide disc gel electrophoresis at pH 9.4. The thus obtained enzyme also showed a single peak at a molecular weight of about 300,000 in gel chromatography with Toyo Pearl 55-F. Further, the thus obtained enzyme showed a single protein band at the location indicating a molecular weight of 49,000 to 50,000 in electrophoresis with a 12% polyacrylamide gel slab containing sodium lauryl sulfate. The yield of the activity was about 9% and the titer showed about 9 units/mg of enzyme. The purification fold was about 70, when that of the crude extract was made 1.

Next, the stability of the thus obtained leucine dehydrogenase was compared with a leucine dehydrogenase obtained from *Bacillus sphaericus* (Comparative Example 1).

As a result, the measurement of the residual activity after heat treatment (incubation) in a 10 mM phosphate buffer solution (pH 7.2) containing 0.01% (v/v) of 2-mercaptoethanol at 70° C. for 10 minutes showed that the leucine dehydrogenase from *Bacillus sphaericus* was 100% inactivated, whereas the leucine dehydrogenase of the present invention did not undergo inactivation even with heat treatment at 70° C. for 10 minutes and still retained about 100% of the activity prior to the treatment even after heat treatment at 70° C. for 30 minutes.

Next, the stability during storage at 4° to 8° C. was examined in a 10 mM phosphate buffer solution (pH 7.2) containing 0.01% (v/v) of 2-mercaptoethanol.

The results are shown in FIG. 1.

In FIG. 1, Curve A indicates Example 1 and Curve B indicates Comparative Example 1. As is evident from FIG. 1, the activity of the leucine dehydrogenase obtained from *Bacillus sphaericus* was decreased to about 50% within 4 days and almost lost within 2 weeks, whereas the leucine dehydrogenase of the present invention still retained almost 100% activity even after the passage of 2 weeks.

Further, the stability during storage at room temperature was also examined. The leucine dehydrogenase obtained from *Bacillus sphaericus* was almost inactivated after 5 days. However, the leucine dehydrogenase of the present invention still retained 90% or more activity even after 10 days passed.

EXAMPLE 2 AND COMPARATIVE EXAMPLE 2

A working solution for the determination of LAP activity contained 15 mM of leucineamide as a substrate, 3 units/ml of the leucine dehydrogenase obtained in Example 1 and 5 mM of NAD+ in 80 mM Tris-hydrochloride buffer solution (pH 8.3). Control sera diluted to various degrees were added to the working solution so as to make the final volume of 1 ml. The reaction was carried out at 37° C. for 3 minutes and a change in absorbancy at 340 nm was measured to calculate the LAP activity.

Figure 2:
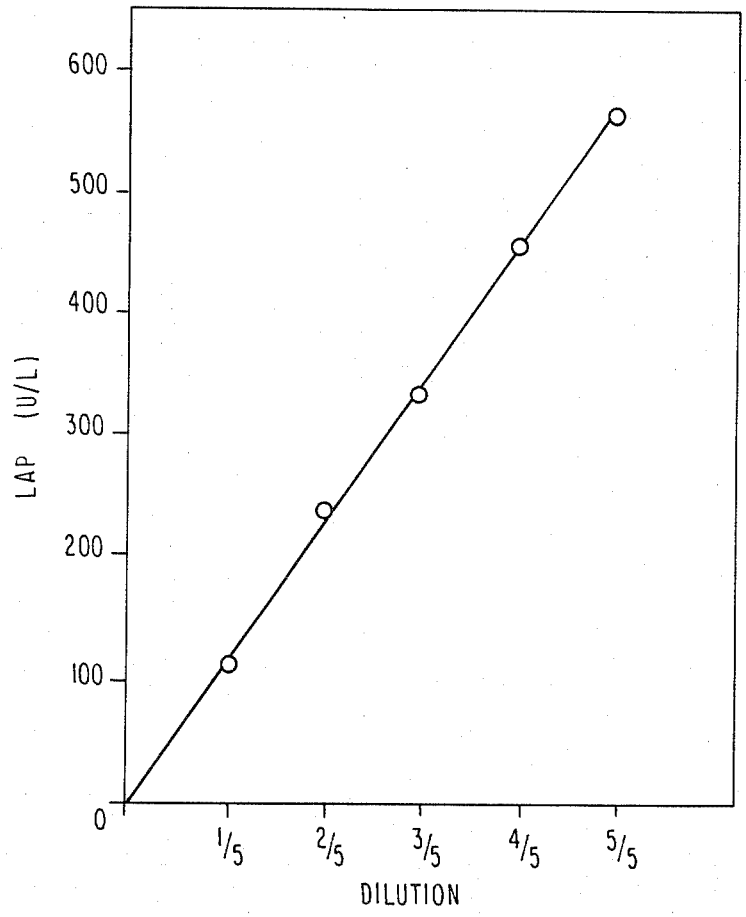
FIG. 2 is a graph showing the relationship between dilution of control serum and the activity of LAP when the composition of the present invention is used to make the reaction liquid 1 ml.

As a result, it was recognized that a good linear relationship was effected, as shown in FIG. 2 and it is thus made clear that the composition of the present invention is effective.

Next, the thus obtained working solution (containing the enzyme) was stored at 4° C. The measurement of the LAP activity after the passage of 6 days indicated an activity value of 98% immediately after the preparation.

On the other hand, a working solution was obtained in a manner similar to Example 2 except that the leucine dehydrogenase obtained from *Bacillus sphaericus*, a microorganism grown at normal temperature, was employed. The working solution was stored at 4° C. and the LAP activity was measured 6 days thereafter. The LAP activity was only 23% of the activity value immediately after the preparation.

That is, it is understood that the composition of the present invention makes it possible to carry out measurement with much better stability and much higher accuracy than in the prior art technique.

While the invention has been described in detail and with reference to specific embodiments thereof, it will be apparent to one skilled in the art that various changes and modifications can be made therein without departing from the spirit and scope thereof.

What is claimed is:

1. A substantially pure leucine dehydrogenase derived from a microorganism having an optimum growth temperature in the range of 50° C. to 85° C., wherein said leucine dehydrogenase is capable of retaining 80% or more of its activity after being incubated in a buffer solution at about 70° C. for about 10 minutes.

2. The substantially pure leucine dehydrogenase as claimed in claim 1, wherein said leucine dehydrogenase is capable of retaining about 90% or more of its activity after being incubated in a buffer solution at about 70° C. for 10 minutes.

3. The substantially pure leucine dehydrogenase as claimed in claim 2, wherein said leucine dehydrogenase is capable of retaining about 10% of its activity after being incubated in a buffer solution at about 70° C. for 10 minutes.

4. The substantially pure leucine dehydrogenase as claimed in claim 1, wherein said microorganism is a member of a genus selected from the group consisting of *Bacillus, Thermoactinomyces, Thermus, Thermomicrobium* and *Carderia*.

5. The substantially pure leucine dehydrogenase as claimed in claim 4, wherein said *Bacillus* is a member of a species selected from the group consisting of *Bacillus*

*stearothermophilus, Bacillus thermoproteoliticus* and *Bacillus acidokaludarius.*

6. The substantially pure leucine dehydrogenase as claimed in claim 5, wherein said *Bacillus* is a strain of the species *Bacillus stearothermophilus.*

7. A composition for assaying leucine amino-peptidase, comprising:
   (1) leucine dehydrogenase derived from a microorganism having an optimum growth temperature in the range of 50° C. to 85° C., wherein said leucine dehydrogenase is capable of retaining 80% or more of its activity after being incubated in a buffer solution at about 70° C. for 10 minutes; and
   (2) a diluent.

8. The composition for assaying leucine amino-peptidase as claimed in claim 7, wherein leucine dehydrogenase is present in an amount in the range of 1 U/ml to 10 U/ml.

9. The composition for assaying leucine amino-peptidase as claimed in claim 7, wherein said leucine dehydrogenase is capable of retaining about 90% or more of its activity after being incubated in a buffer solution at about 70° C. for 10 minutes.

10. The composition for assaying leucine amino-peptidase as claimed in claim 9, wherein said leucine dehydrogenase is capable of retaining about 10% of its activity after being incubated in a buffer solution at about 70° C. for 10 minutes.

11. The composition for assaying leucine amino-peptidase as claimed in claim 7, wherein said microorganism is a member of a genus selected from the group consisting of *Bacillus, Thermoactinomyces, Thermus, Thermomicrobium* and *Carderia.*

12. The composition for assaying leucine amino-peptidase as claimed in claim 11, wherein said *Bacillus* is a member of a species selected from the group consisting of *Bacillus stearothermophilus, Bacillus thermoproteoliticus* and *Bacillus acidokaludarius.*

13. The composition for assaying leucine amino-peptidase as claimed in claim 12, wherein said *Bacillus* is a strain of the species *Bacillus stearothermophilus.*

14. A process for producing leucine dehydrogenase comprising the steps of:
   (1) providing a microorganism having an optimum growth temperature in the range of 50° C. to 85° C.;
   (2) culturing said microorganism; and
   (3) harvesting leucine dehydrogenase from said cultured microorganism,
wherein said leucine dehydrogenase is capable of retaining 80% or more of its activity after being incubated in a buffer solution at about 70° C. for 10 minutes.

15. The process for producing leucine amino-peptidase as claimed in claim 14, wherein said leucine dehydrogenase is capable of retaining about 90% or more of its activity after being incubated in a buffer solution at about 70° C. for 10 minutes.

16. The process for producing leucine amino-peptidase as claimed in claim 15, wherein said leucine dehydrogenase is capable of retaining about 10% of its activity after being incubated in a buffer solution at about 70° C. for 10 minutes.

17. The process for producing leucine amino-peptidase as claimed in claim 14, wherein said microorganism is a member of a genus selected from the group consisting of *Bacillus, Thermoactinomyces, Thermus, Thermomicrobium* and *Carderia.*

18. The process for producing leucine amino-peptidase as claimed in claim 17, wherein said *Bacillus* is a member of a species selected from the group consisting of *Bacillus stearothermophilus, Bacillus thermoproteoliticus* and *Bacillus acidokaludarius.*

19. The process for producing leucine amino-peptidase as claimed in claim 18, wherein said *Bacillus* is a strain of the species *Bacillus stearothermophilus.*

* * * * *